United States Patent [19]

Meilland

[11] Patent Number: Plant 7,347

[45] Date of Patent: Oct. 9, 1990

[54] ROSE PLANT—MEINABRON VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 321,143

[22] Filed: Mar. 9, 1989

[51] Int. Cl.[5] ..... A01H 5/00

[52] U.S. Cl. ..... Plt./8

[58] Field of Search ..... Plt. 8

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which abundantly and continuously forms elegant long lasting blossoms. The blossoms are a true white and exhibit an attractive form even when fully open. The plant is well suited for pot forcing, roots with ease, and forms particularly pleasing ornamentation when grown as a flowering pot plant either indoors or outdoors.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Meidonq variety (non-patented in the United States). The male parent (i.e., the pollen parent) of the new variety was the product of the pollination of the Darling variety (non-patented in the United States) by the Jack Frost variety (U.S. Plant Pat. No. 2,522) The parentage of the new variety can be summarized as follows: *Meidonq*×[*Darling*×*Jack Frost*].

The seeds resulting from the above pollination were sown and plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive long lasting double blossoms which are white in coloration and possess firm petals,
(b) forms green adult wood,
(c) exhibits a vigorous growth habit,
(d) exhibits a bushy configuration, and
(e) is well suited for pot forcing.

The new variety is particularly noteworthy for its elegant white blossoms and vigorous rate of growth.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meinabron variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during April while growing on their own roots outdoors at Cannet-des-Maures, Var, France.

Figures 1, 2, 3, 4, 5, 6, 7, 8, 9, 10, 11, 12, 13, 14, 15, 16:
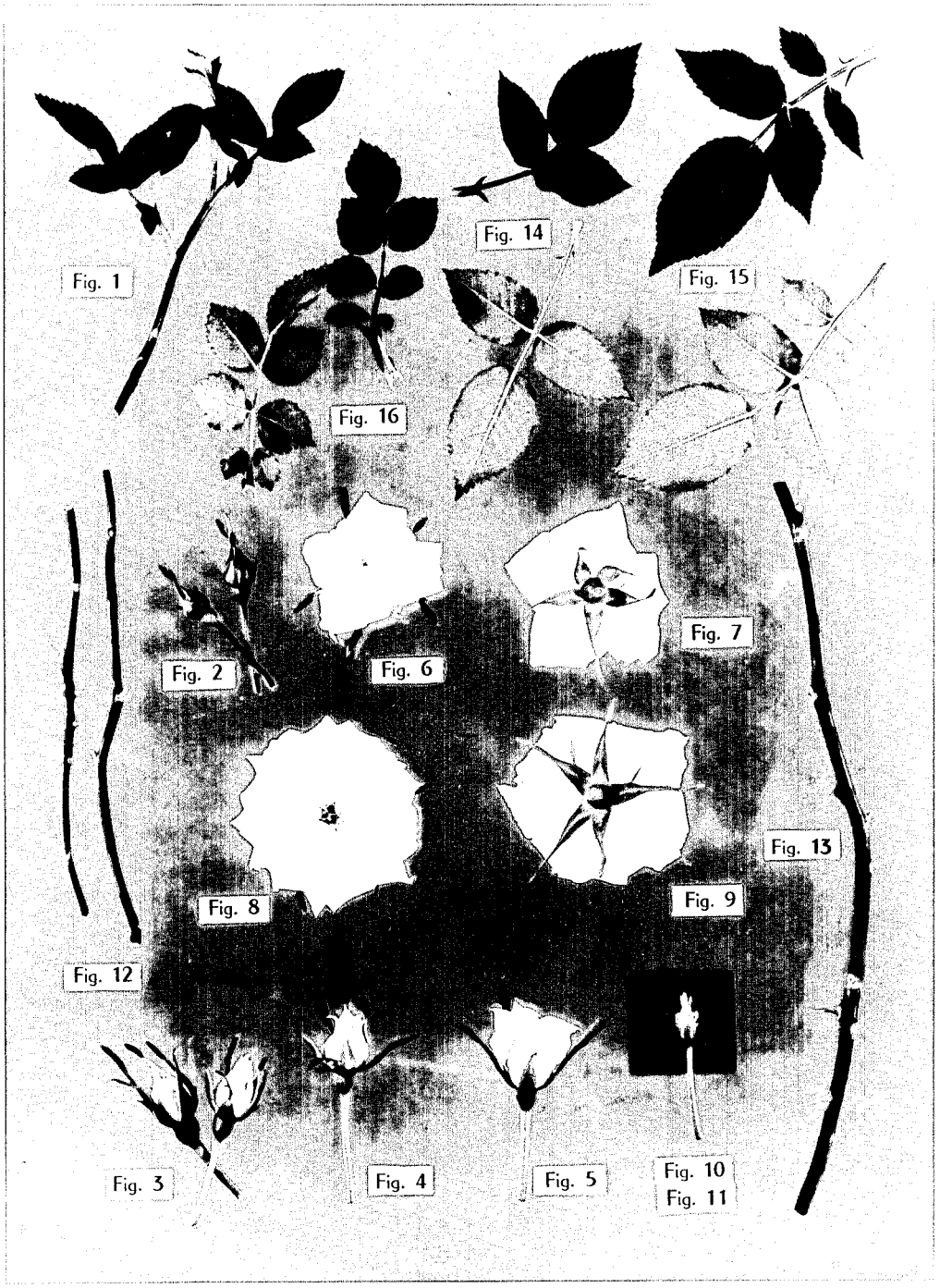
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.

FIGS. 10/11 illustrates a specimen of a floral receptacle showing the arrangement of the stamens and pistils (sepals removed);

FIG. 12 illustrates specimens of two flowering stems;

FIG. 13 illustrates a specimen of a flowering stem of larger diameter;

FIG. 14 illustrates specimens of leaves with three leaflets with the upper surface being shown on the top and the under surface being shown on the bottom;

FIG. 15 illustrates specimens of leaves with five leaflets with the upper surface being shown on the top and the under surface being shown on the bottom; and FIG. 16 illustrates specimens of leaves with seven leaflets with the upper surface being shown on the right and the under surface being shown on the left.

DETAILED DESCRIPTION

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety during April while growing on their own roots outdoors at Cannet-des-Maures, Var, France.

Class: Miniature.

Plant:

*Height.*—Approximately 25 to 30 cm. on average.

*Habit.*—Bushy.

Branches:

*Color.*—Young stems: medium green, Yellow-Green Group 146B, more or less suffused with reddish brown. Adult wood: medium green, Yellow-Green Group 146B.

Leaves:

*Petioles.*—Upper Surface: reddish brown on young foliage and medium green on adult foliage with more or less glandular edges. Under surface: light green with some small thorns.

*Leaflets.*—Number: 3, 5 and 7 (most often). Shape: elliptic, lanceolate. Serration: simple and regular. General appearance: ample and dense with semi-dull aspect. Color (young foliage): Upper surface: lettuce green, Yellow-Green Group 144A with a very large suffusion of reddish brown. Under surface: lettuce green, Yellow-Green Group 144A with a very large suffision of reddish brown. Color (adult foliage): Upper surface: medium green, Green Group 137A. Under Surface: light green, Green Group 137C.

Inflorescence:

*Number of Flowers.*—Approximately 1 to 4 per stem.

*Peduncle.*—Straight, rigid, light green and spotted with reddish brown, its length is approximately 4 cm. on average.

*Buds.*—Shape: conical. Length: approximately 1.5 to 2 cm. on average. Color upon opening: Upper Surface: white, White Group 155B, more or less greenish on external petals. Under surface: white, White Group 155B, more or less greenish on external petals.

*Flower.*—Form: flatted cup-shaped. Diameter: approximately 5.5 cm. on average. Color (when opening begins): Upper surface: white, White Group 155B, lightly suffused with pale primrose yellow, Yellow Group 4D in the center. Under surface: white, White Group 155B. Color (when blooming): Upper surface: white, White Group 155B. Under surface: white, White Group 155B. Color (at end of blooming): Upper surface: white, White Group 155B. Under surface: white, White Group 155B. Fragrance: none. Lasting quality: long. Petal number: approximately 85 to 90 on average. Petal form: oval on external petals and very narrow and lanceolate on the inside petals.

Petal texture.—Firm. Petal drop: good. Stamens: very few; however, there is often a vegetative center.

Development:

*Vegetation.*—Vigorous.

*Blooming.*—Abundant and continuous.

*Aptitude to bear fruit.*—Poor.

*Resistance to diseases.*—May sometimes be sensitive to powdery mildew.

I claim:

1. A new and distinct variety of Miniature rose plant characterized by the following combination of characteristics:

(a) forms in abundance on a continuous basis attractive long lasting blossoms which are white in coloration and possess firm petals, (b) forms green adult wood, (c) exhibits a vigorous growth habit, (d) exhibits a bushy configuration, and (e) is well suited for pot forcing;

substantially as herein shown and described.

* * * * *